United States Patent
Osypka

(10) Patent No.: US 8,172,872 B2
(45) Date of Patent: May 8, 2012

(54) DEVICE FOR CLOSING AN OPENING LOCATED IN A HEART SEPTUM

(76) Inventor: Peter Osypka, Rheinfelden-Herten (DE)

( * ) Notice: Subject to any disclaimer, the term of this patent is extended or adjusted under 35 U.S.C. 154(b) by 982 days.

(21) Appl. No.: 12/159,694

(22) PCT Filed: Dec. 21, 2006

(86) PCT No.: PCT/EP2006/012413
§ 371 (c)(1), (2), (4) Date: Jun. 30, 2008

(87) PCT Pub. No.: WO2007/079952
PCT Pub. Date: Jul. 19, 2007

(65) Prior Publication Data
US 2009/0012557 A1 Jan. 8, 2009

(30) Foreign Application Priority Data
Dec. 28, 2005 (DE) .......................... 10 2005 062 657

(51) Int. Cl.
*A61B 17/08* (2006.01)
*A61M 31/00* (2006.01)
(52) U.S. Cl. .................. 606/213; 606/215; 606/218
(58) Field of Classification Search .................. 606/213, 606/215, 218, 158, 191; 604/160, 256; 607/120, 607/122; 623/1.11; 600/374
See application file for complete search history.

(56) References Cited

U.S. PATENT DOCUMENTS

| 6,056,760 A * | 5/2000 | Koike et al. ............ 606/148 |
| 6,669,707 B1 | 12/2003 | Swanstrom et al. |
| 2002/0165589 A1 | 11/2002 | Imran et al. |
| 2002/0169377 A1 | 11/2002 | Khairkhahan et al. |
| 2004/0176788 A1 | 9/2004 | Opolski |
| 2005/0119675 A1 | 6/2005 | Adams et al. |
| 2005/0177181 A1 * | 8/2005 | Kagan et al. ............ 606/151 |

FOREIGN PATENT DOCUMENTS

| EP | 0856285 | 8/1998 |
| JP | 7171173 | 7/1995 |
| WO | 2004043272 | 5/2004 |
| WO | 2004091716 | 10/2004 |
| WO | 2004100812 | 11/2004 |
| WO | 2005065412 | 7/2005 |

* cited by examiner

*Primary Examiner* — Vy Q Bui
(74) *Attorney, Agent, or Firm* — Volpe And Koenig, P.C.

(57) ABSTRACT

A device (1) for closing an opening (2) in a septum (4) of a heart (3) comprises: at least two closure elements (12) with threads (8) for closing the opening (2), a feed catheter (5) for insertion of the closure element (12) into the heart (3), a puncture cannula (6), a stylet (7) for pushing the closure element (12) out of the puncture cannula (6), and a screw catheter (10) having a coil (11) for penetration the edge of the opening (2). The puncture cannula (6) and the elements (12) can be moved through the screw catheter (10) and the coil (11). If the edges of the opening (2) overlap, a lobe (15) away from the feed catheter (5) can be kept in place with a second coil (111), or a suction tube (16) during placement of the anchor (12).

22 Claims, 15 Drawing Sheets

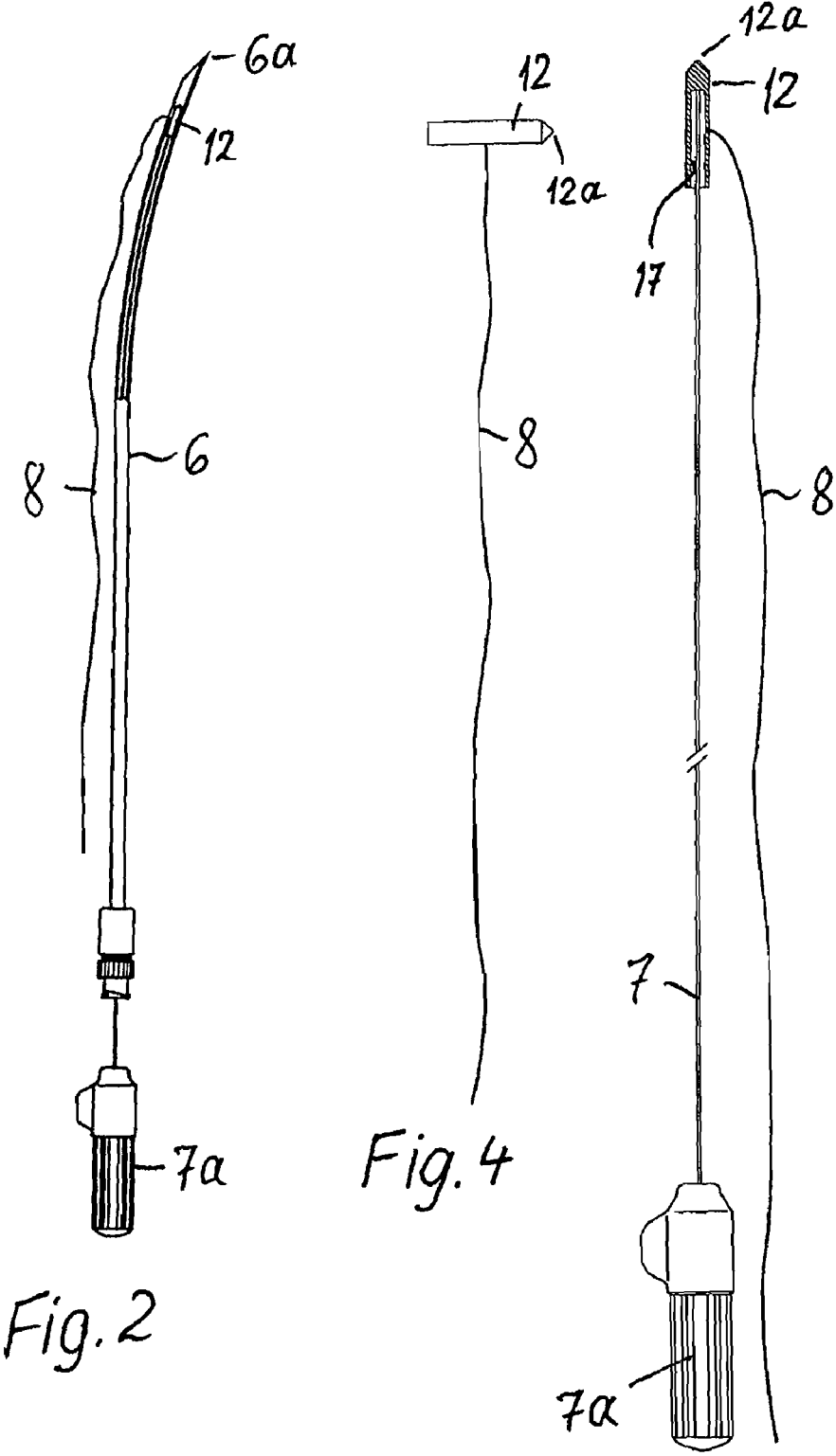

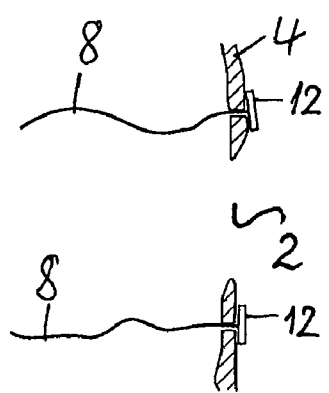
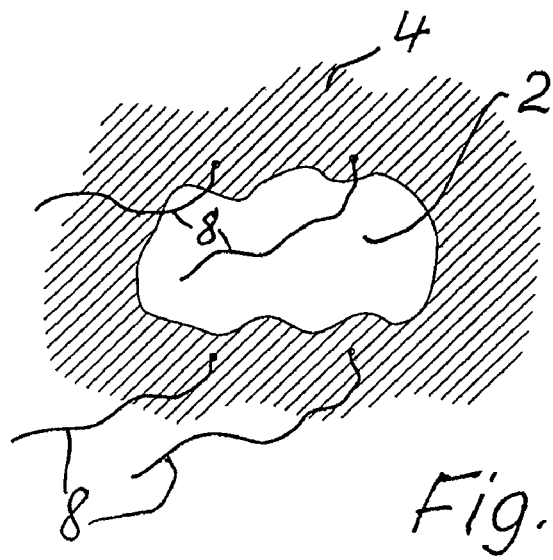
Fig. 14　　　　　Fig. 15
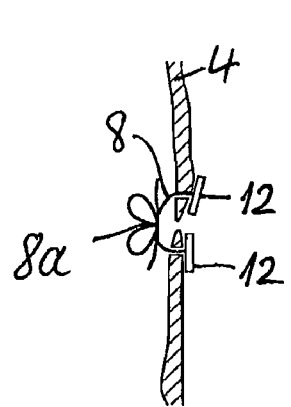
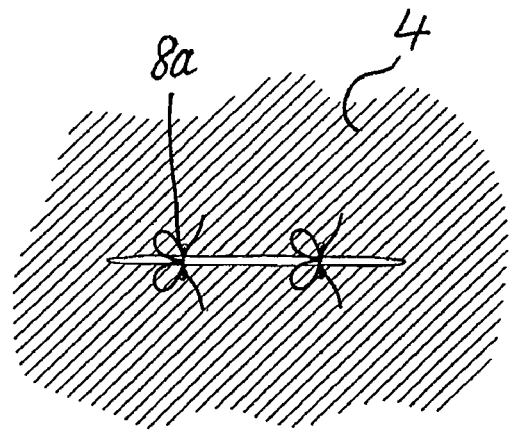
Fig. 16　　　　　Fig. 17

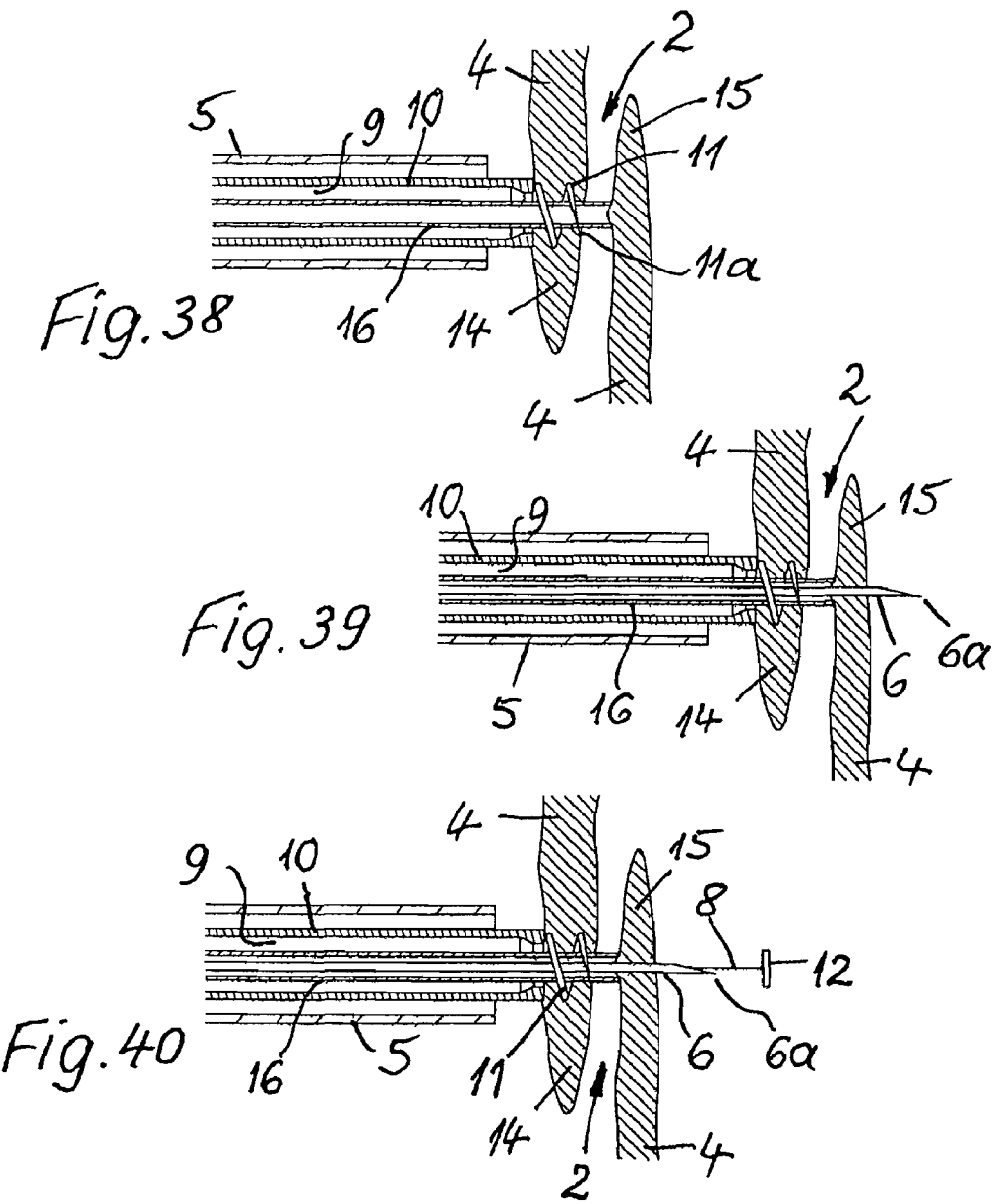

DEVICE FOR CLOSING AN OPENING LOCATED IN A HEART SEPTUM

BACKGROUND

The invention relates to a device for closing an opening in a septum located in the heart between two heart chambers, particularly between the right atrium and the left atrium, having a closing element, a feed catheter for the transvenous introduction of the closing element into the interior of the heart and having a puncture cannula as well as a tool or stylet to displace the closing element out of the distal end of the puncture cannula after its piercing through the edge or the neighboring area of the opening located in the heart septum, with at least two individual elements being provided as closing elements, having pulling means or threads, which can be pulled together, connected, and/or knotted for closing the opening in the position of use.

Such a device is known from U.S. Pat. No. 6,056,760. Using the puncture cannula, the edge region of the opening in the heart septum is pierced with the help of the puncture cannula and then an anchoring element with an anchor pin arranged perpendicular in reference to the pulling means is fixed through the interior longitudinal cavity of the puncture cannula such that the pulling means are knotted to each other and thus the edges of the opening can be pulled together and closed. Here, it must be assumed that the heart tissue of the heart septum is elastic in the area of the opening to such an extent that even a very sharply cut puncture cannula deflects the edge region of the heart septum rather than penetrating it. It is a concern that the edge region of the opening is missed, when the puncture cannula engages, thereby preventing a penetration of the puncture cannula and much less an insertion or piercing of the holding element in the edge region of the opening of the heart septum.

This known device is even less suited for closing an opening in a heart septum formed by two overlapping tissue flaps in the heart.

SUMMARY

The object of the invention is therefore to provide a device of the type mentioned at the outset by which closing elements in the form of pin-shaped anchors are created, embodied as individual elements, with their central area being fastened to pulling means or threads or perhaps a wire or a line, by which said anchor can be fastened securely in the edge region of an opening of a heart septum.

In order to attain this object the device defined at the outset is provided with at least one screw catheter that is provided with an interior feed channel and can be inserted into a guide catheter with, at its distal end, at least one helical screw being provided that can be screwed into the edge region of the opening in the heart septum. The lumen or the open interior cross-section of the screw catheter and the helical screw or the helical screws being selected of such a size that the puncture cannula with the anchor included therein, allocated to the closing element, is displaceable in reference thereto and through said interior cross-section as well as by the helical screw or helical screws.

Using such a device allows first to screw the helical screw or, if applicable, two or more helical screws, off-set in the circumferential direction of equal size and identically aligned, and showing an identical angular incline of the screw catheter that can be inserted transvenously into the heart, into the edge region of the opening in the heart septum at the location where the anchor of the closing element shall be mounted. Here, the helical screw can serve as a counter-fastener when the puncture cannula is pierced into this edge region so that the edge region of the opening of the heart septum cannot be deflected when the puncture cannula or the anchor is piercing it.

The closing element can therefore comprise essentially two anchors in the minimum case that can be mounted at opposite edges of the opening to be closed or edges facing away from each other, with its pulling means in the position of use being connected to each other and pulled together, so that hereby the edges of the opening are also pulled towards each other, or if applicable slightly overlapping, causing the opening to be closed and allowing it to grow shut. Here during the piercing with the puncture cannula and/or the anchor pin the heart septum is prevented from deflecting by the helical screw or helical screws of the screw catheter in order for the anchor or anchor pins to securely penetrate the heart septum. The helical screw therefore forms a practical counter bearing at the heart septum to compensate any forces developing when the heart septum is being pierced.

Here, it is beneficial that the screw catheter in the position of use can be fixed or captured at its proximal end and the helical screws, as already mentioned, serve as counter bearings and for counteracting the force of the puncture cannula acting upon the heart septum when piercing the edge area of the opening. The same applies if instead of puncture cannula or additionally thereto the anchor pin penetrates the heart septum when being pushed out of the respective cannula. The screw catheter can therefore be fixed or held in a position relative to the feed catheter in the position of use, after it previously had been displaced in reference to said feed catheter and through it to its position of use. Here it must be mentioned that the application of at least two anchors can also be beneficially provided with two guiding catheters or screw catheters having helical screws.

The helical screws can be provided with at least one or two, particularly approximately one and one half windings and in the position of use encompass the point to be punctured next to the opening in the heart septum. Using at least one winding or slightly more it is ensured that the entire area to be punctured or pierced is captured at its perimeter by the helical screw so that the holding forces of the helical screw can be transferred rather evenly to said area to be pierced and a partial area cannot deflect from the penetrating forces, which would be possible in case of less than one full winding of the helical screw.

The incline of the helical screw(s) can be selected such that its/their tip(s) in the position of use protrude from the side of the heart septum facing away from the feed catheter. This results in that the entire thickness of the heart septum is used to anchor the helical screw and to compensate the counter forces to be accepted thereby.

The shaft of the screw catheter transferring the screw force may be flexible but not elastic or only to a slight extent. This way, the screw catheter can well adjust to the changing directions during its feeding and still transfer very well the counter-forces developing during the puncturing process.

It is beneficial for the wall of the screw catheter to comprise one or more wire, particularly forming a closed helix. Such a catheter wall comprising one or more coiled wires can sufficiently transfer an axial force, on the one hand, and on the other hand, be of sufficient flexibility and pliability when being fed through blood vessels into the interior of the heart.

At the distal end of the helical screw, a cross-sectional constriction or a stop acting as a retention mechanism for the puncture instrument may be provided in front of the helical screw, with said stop limiting the length the puncturing instrument projects from the screw catheter and in reference to the helical screw. This ensures even better that a puncture instrument, when piercing the heart septum, cannot reach the opposite myocardium and injures it. Due to the fact that the puncturing instrument may represent a cut cannula or a sharp mandrin or an injection needle the risk is avoided that septum or the dividing heart wall opposite the heart septum, for example the atrium myocardium in the left atrium is injured when the entire device is used appropriately.

A counter stop may be arranged at the puncturing instrument at a distance from its tip in cooperation with the retention mechanism or stop limiting the projection length of the puncture instrument out of the screw catheter in the position of use.

At least two anchors provided with pulling means can be mounted as locking elements, having a distance form each other in the edge region of the opening of the heart myocardium via a puncture cannula and their pulling means can be or are knotted to each other in the position of use.

The modified, useful embodiment of the device according to the invention, primarily suited to close an opening formed by two overlapping tissue flaps in the heart, can be provided with a second screw catheter, which fits into the first screw catheter and which can be pushed through it and is rotational in reference thereto, whereby the first screw catheter, having at least one helical screw, can be screwed into a tissue flap located closer to the guiding catheter and subsequently the second screw catheter can be screwed through this tissue flap and the first one into the second tissue flap, with the lumen or the open interior cross-section of the second screw catheter and its at least one helical screw being selected of such a size that the puncture instrument with the included anchor, allocated to the closing device, is displaceable in reference thereto and through said interior cross-section and the second helical screw(s) into the area behind the second tissue flap.

Using the device according to the invention it is therefore possible, by the embodiment having two screw catheters arranged in reference to each other and inserted into each other, to close an opening in the heart in which two tissue flaps of the myocardium are located behind or over each other, but are not grown together or connected. This way, a PFO-closure (Patent Foramen Ovale) can be formed, in turn using the principle to grasp the respective edge areas or areas adjacent to the existing opening with the help of helical screws, namely to grasp the tissue flaps and to hinder any deflection. Here, a tissue flap facing away from the guiding catheter can even be pulled against the tissue flap located closer in reference to the guiding catheter with the help of the second helical screw such that both tissue flaps can already be positioned abutting tightly during the mounting of the closure element or elements and the anchor(s).

Here, it is beneficial if—additionally—the second screw catheter can be fixed or engaged at its proximal end and its helical screw(s) serve as a counter stop to compensate the force acting upon the flap when the puncture cannula pierces the rear tissue flap, located further apart from the guiding catheter.

This way it is possible to close an opening in a heart septum, in which two tissue flaps arranged over top of each other or behind each other form said opening and by an anchoring using a closing element, i.e. a PFO-closure, are triggered to grow together.

A modified embodiment of the device, particularly for closing an opening formed by two tissue flaps arranged in the heart above or behind each other such that a suction tube or hose is provided, which is displaceable through the screw catheter and its helical screw(s) and a puncture opening into the first tissue flap facing the guiding catheter to the second tissue flap overlapping the first flap and can be connected to a vacuum source at its proximal end. Instead of a second screw catheter, which is displaceable through the first screw catheter, a suction tube or hose may be provided by which a vacuum and/or negative pressure can act upon the rear tissue flap, seen in the direction of the treatment, in order to allow the counter-force to be compensated with the help of an anchor during puncturing or piercing.

The suction tube or the suction hose can have an interior cross-section, through which the puncture instrument and/or the puncture cannula with the anchor included therein and allocated to the closing device can be displaced in reference thereto and through said interior cross-section as well as through the second tissue flap.

The suction tube or the suction hose can be fixed or engaged at its proximal end and due to the vacuum affecting it serve as a counter-fastener and compensate the force said puncture cannula acts upon them when piercing the rear tissue flap.

At least two anchors can be provided with pulling means mounted adjacent to each other as closures or closing elements and be connectable and/or knotted together at their ends facing away from the anchors.

In the various embodiments of the device according to the invention it is beneficial if the anchors are pin-shaped and can pierce or be guided through the heart septum, as attachment sites for a tool or a stylet have a deformation at the end opposite the tip that can be pierced or guided through, in particular a recess open at the end opposite the tip and ending inside the pin-like anchor, which can be detachably coupled with the tool, with the tool or the stylet particularly fitting into the recess, with the pulling means each engaging approximately at their middle between the two ends of the pin-like anchor.

In the position of use, the respective anchor with its pulling element or pulling means forms a T-shape, because the pin-like anchor is displaceable in reference to the pulling means. Therefore, the anchor can first be completely moved through the heart tissue via the tool or the stylet and then be supported at the rear side facing away from the feeding side by a redeflection in reference to the pulling means, while the pulling means or the thread extends back through the opening, which developed by the piercing or the penetration. This way, in the position of use, the entire length of the pin-shaped anchor is available as the anchoring and resistance area so that this anchor may be appropriately small, which simultaneously almost excludes any risks for potential embolisms.

In a modified embodiment the respective anchor can be flexible or folding in reference to the engagement site of the pulling means and against its direction of insertion. Therefore, this anchor can be pushed through the puncture cannula and the heart tissue, with the areas located at both sides of the engagement site of the pulling means being bent or folded towards each other. When the heart tissue has been passed, these two areas can unfold again and contact the tissue in the sense of anchoring.

The chance according to the invention to prevent the deflection of the heart tissue during the mounting of anchors in any type of opening in a heart septum, using at least one helical screw or a suction tube or the like, and thus to facilitate the piercing of the respective area of the heart septum both ASD-closures as well as PFO-closures can be mastered, in which the helical screws used are adjusted or supplemented accordingly. ASD represents Atrial Septal Defect. PFO represents Patent Foramen Ovale.

For the above-described devices and applications it is beneficial for the puncture cannulas to accept the tool and the anchor in its interior and to accept the anchor in its entirely or partially, with the pulling element or the thread exiting the distal end of the puncture cannula in an arrangement of the anchor therein and arranged at the outside of the puncture cannula. The respective anchor can therefore first be inserted at least partially at the distal end of the puncture cannula, while its pulling means or pulling element remains at the outside of said puncture cannula. Said cannula can be displaced by the feed catheter into its position of use, where the anchor then with the help of the tool or stylet can pierce, or be pushed out of the distal end of the puncture cannula, immediately into the edge of the opening of the heart septum or a puncture cannula penetrating the heart septum can be transported by a guiding catheter behind said heart septum, seen from the guiding catheter.

Here, the puncture cannula can protrude with its tip the respective anchor held by it, initially, such that it can puncture or punch the septum in the heart at the edge of the opening to be closed, where subsequently the anchor is to be pierced or pushed through or placed through. Thereafter, this anchor is pushed by a tool out of the puncture cannula and/or the puncture cannula is retracted in reference thereto, fixing the anchor with the help of the tool in reference thereto.

Advantageously, when using the device and/or the set comprising the individual parts mentioned, the mounting of the anchor can be immediately observed with imaging methods.

A particularly beneficial embodiment of the device according to the invention and/or the set forming this device is that the anchor and the pulling means can comprise a non-metal material, particularly plastic, or a bio-compatible material. Here, the use of bio-compatible plastics is particularly beneficial.

Even if the opening in the heart septum to be closed is relatively large, at least three or four anchors and pulling means can be provided, allowing the use of the device as an ASD or PFO-closure.

Particularly the use of the device as an ASD-closure may be beneficial particularly for relatively large openings in the heart septum, when the closing device is provided with or comprises at least two anchors each having pulling means engaging them and at least one closing plate, which in its edge region has holes for the pulling means to pass through and through which the pulling means or threads extend on the rear side of the closing plate in a position of use facing away from the opening to be closed, where they are connected or connectable or knotted or can be knotted. Therefore, if the opening to be closed is so large that pulling the edges together to close them is insufficient, the device and/or the set forming the device may include the closing plate mentioned, which no longer requires a mutual approach of the opening edges or reduced the extend of said approach of the edges.

Here, it is beneficial if at least three or four anchors and pulling means and a closing plate are provided as a closing device. The closing plate can then be well guided by the pulling means and be held thereby.

The closing plate may comprise bio-compatible and/or non-metal materials.

Here, it is beneficial if the closing plate and several anchors with pulling means are provided as the closing device and that two anchors each and their pulling means can be connected or connectable or knotted or can be knotted to each other in the position of use.

It is therefore possible to connect or knot together the pulling elements or pulling means of those anchors on the side of the closing plate facing away from the opening of the heart septum which are adjacent to each other such that the connected pulling elements or pulling means in the position of use extend over the edge of the opening in the heart septum at the rear side of the closing plate. With an accordingly good affect the closing plate, in its position of use, is compressed to the respective edge of the opening and can ensure the desired sealing as an ASD-closure. Here it proves advantageous for the anchor, pulling means, and the closing plate to be comprised of a bio-compatible material, particularly plastic, and based on a certain inert elasticity can be well adjusted to the surface in the edge region of the opening of the heart septum.

It must also be mentioned that the respective anchor can also be a bendable, for example an angular or hook-shaped part, which, by a pulling force against the direction of insertion in reference to the pulling means or thread opens or spreads and/or blocks the retraction of the pulling means or thread through a hole or a section of the heart septum.

Primarily, from combinations of individual or several of the above-described features and measures a device and/or a set results for closing an opening in a septum located in the heart in form of an ASD or PFO closure, in which the actual closing unit comprises very few parts with small amounts of material, in which the use of metal can be avoided entirely for the parts remaining in the heart. This way, the risk of an embolism can be considerably reduced which could be caused by such a closing unit or an equivalent closure. Due to the fact that the anchor and its pulling means can be relatively small parts, they each can be easily brought successively via one or more puncture cannulas to their respective position of use by a catheter and screw catheter(s).

BRIEF DESCRIPTION OF THE DRAWINGS

In the following embodiments of the invention are described in greater details using the drawings. They show in a partially considerably diagramed illustration:

FIG. 2: a puncture cannula of the device according to the invention, displaceable through the feed catheter and the screw catheter located therein, the contains one of at least two anchors arranged individually behind one another at their distal end, which anchor is provided with a pulling means or pulling element extending at the exterior of the puncture cannula, and with a tool, by which the anchor can be pushed out of the puncture cannula and can be pushed through the edge region of an opening to be closed, FIG. 3: in an enlarged view of, the engagement of the tool at the anchor without the puncture cannula accepting the anchor and the tool, with the anchor being shown in a longitudinal cross-section, FIG. 4: an anchor as a part of a device according to the invention and/or a set according to the invention with its pulling element or pulling means.

FIG. 14: in a schematic representation, a cross-section of the edges of the opening in the heart septum after the mounting of at least two or perhaps three or four or more anchors, with the pulling means extending from the anchors through the heart septum, FIG. 15: a view of the opening in the heart septum from the side facing away from the anchors with four pulling means, FIG. 16: an illustration according to FIG. 14, after anchors mounted at opposite opening edges have been pulled together with the help of their pulling means and have been knotted such that the edges of the opening have largely approached each other, FIG. 17: a view according to FIG. 16 after the connection and pulled together of the pulling elements or pulling means of the anchors, thus practically closing the opening entirely and/or allowing it to grow shut, FIG. 34: an illustration according to FIG. 33 after the puncturing and dilating and after the insertion of a second screw catheter through the first tissue flap and after its helical screw has been screwed into the rear tissue flap, in the direction of insertion, FIG. 35: an illustration according to FIGS. 33 and 34 during the insertion of a puncture element or a puncture cannula through the interior lumen of the second screw catheter and its helical screw and thus through the rear tissue flap in the direction of insertion, FIG. 36: an illustration according to FIG. 35 after the anchor and its pulling means have been pushed out, and FIG. 37: the mutual connection of at least two pulling means allocated to two anchors with the help of a knot and by the two tissue flaps contacting each other, FIG. 38: an illustration according to FIG. 34, with instead of the second screw catheter a suction tube or hose being pushed by the screw catheter and the helical screw according to FIG. 33 up to the rear tissue flap, in the direction of insertion, and hindering it from deflecting from the front tissue flap by a vacuum, FIG. 39: an illustration according to FIG. 35, in which a puncture instrument with an anchor holding it being pierced through the rear tissue flap in the direction of feed, with the suction tube holding said tissue flap against the penetrating force, as well as FIG. 40: an illustration according to FIG. 36 after the anchor has been pushed out, which serves to close the opening according to FIG. 37.

DETAILED DESCRIPTION OF THE PREFERRED EMBODIMENTS

Figure 1:
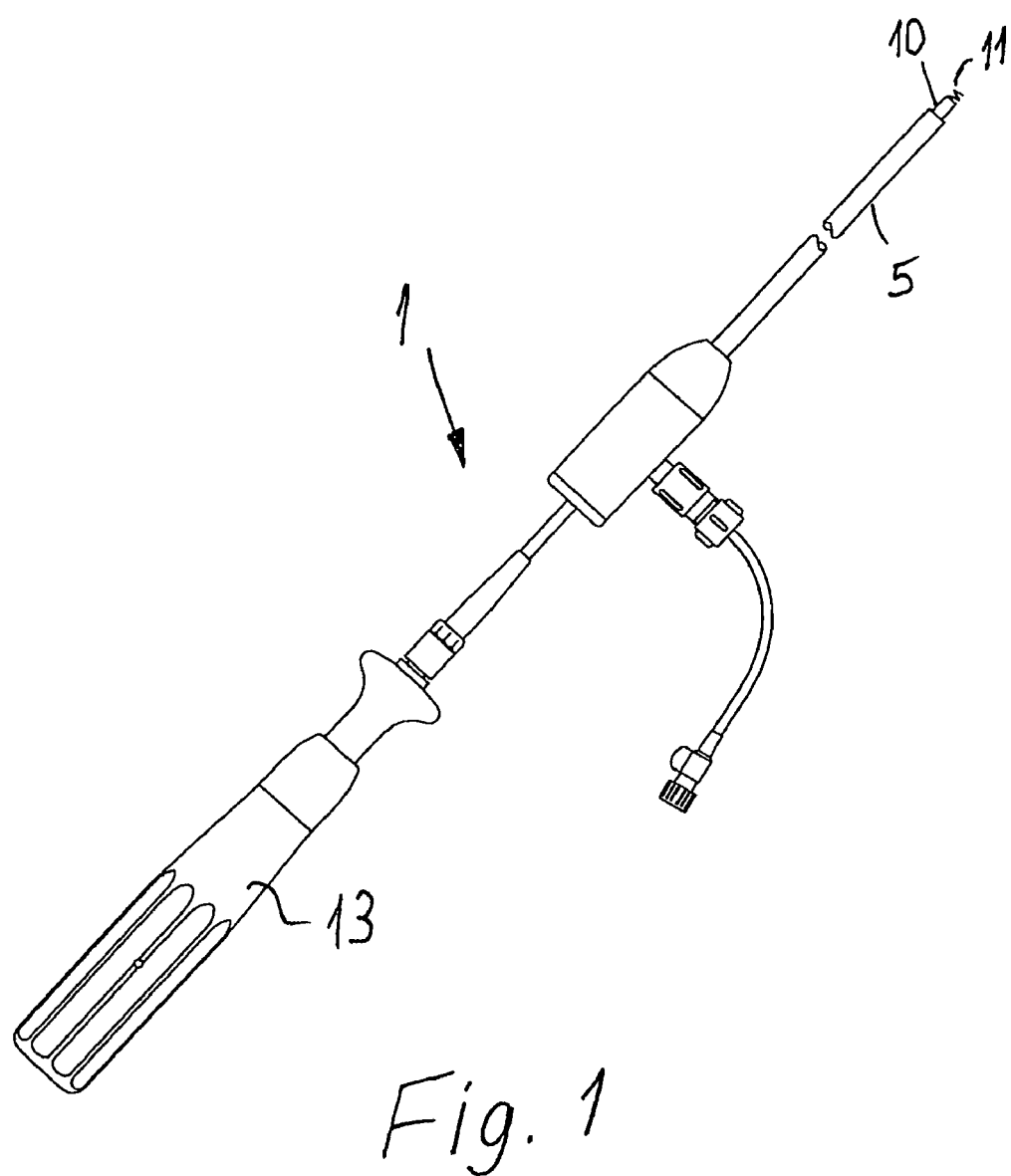
FIG. 1: a side view of a device according to the invention with a feed catheter and a screw catheter arranged therein and displaceable through it, with its proximal end projecting from the guiding catheter towards the back and provided with a holding handle for displacing and turning, while at the distal end of this screw catheter a helical screw is provided, which projects in the shown position from the feed catheter.
Figure 5:
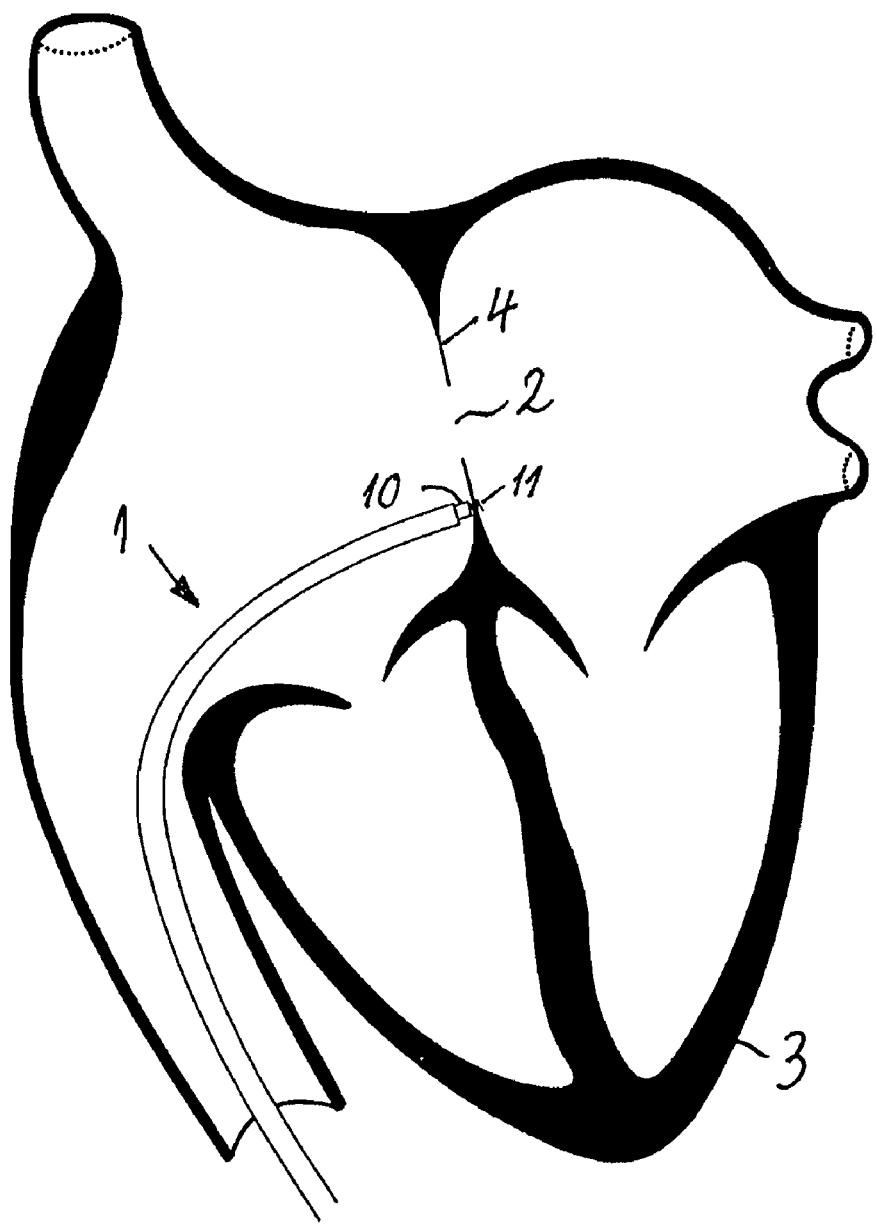
FIG. 5: a cross-section through a heart and the left and the right atria, with a guiding catheter and a screw catheter being introduced transvenously into the right atrium and approaching, with its mouth, the septum such that the helical screw can be screwed into it and/or has already been screwed into it.

A device, in its entirety marked 1, which can also be considered a set, serves to close an opening 2 in a heart 3 between two heart chambers, particularly a septum 4 located between the right atrium and the left atrium with a closing element to be explained in greater detail using the embodiments.

Parts and objects equivalent with regard to their function are marked with identical reference characters, even if they are embodied differently.

The device 1 is here embodied as an ASD-closing device according to FIGS. 1 through 32 and as a PFO-device according to FIGS. 33 through 40, where the differently embodied devices 1 have equivalent parts with regard to their function marked with identical reference characters.

According to FIG. 1, a feed catheter 5 for the transvenous introduction of the respective closing element into the interior of the heart 3 is a component of the respective device 1 and/or the set forming it. Further, the respective device 1 is provided with a puncture cannula 6 as well as a tool 7 or a stylet for pushing the closing element to be explained in greater detail out of the distal end of the puncture cannula 6 after its penetration through the edge or the neighboring section of the opening 2 located in the heart septum 4, with at least two individual elements being provided as closing elements, provided with pulling means 8 or threads, in the following also called "pulling elements", which according to FIGS. 16, 17, 21, 22, or 25 and 26 can be pulled together to close the opening 2 in the position of use, connected, and/or knotted.

In all embodiments the respective device 1, which may also be considered a set, is provided with at least one screw catheter 10 that can be inserted into the feed catheter 5 having an interior feed channel 9, with a helical screw 11 being provided at its distal end that can be screwed into the heart septum 4 in the edge region of the opening 2, with the lumen or the open interior cross-section of the screw catheter 10 and its helical spring 11 being selected of such size that the puncture cannula 6 together with the anchor 12 allocated thereto and initially located therein, being displaceable in reference thereto and through said interior cross-section as well as through the helical screw 11. Here, several, preferably two identical helical screws 11 may be provided, off-set in reference to each other in the circumferential direction, by which the tissue can be engaged even more efficiently.

An essential part of the device 1 is therefore the screw catheter 10 provided with the interior feed channel 9 that can be inserted into the feed catheter or the guiding catheter 5 and passing through it, which is discernible in FIG. 1 having its two ends projecting from the guiding catheter 5. Further, the distal end of this screw catheter 10 and its helical screw 11 are shown in a side view in FIG. 7 and in a longitudinal cross-section, for example in FIGS. 8 through 10 for one embodiment and in FIGS. 33 through 40 for two additional embodiments. Here, it is also discernible that the helical screw 11 provided at the distal end of the screw catheter 12, which can be screwed into the septum and/or the separating wall of the heart 4, has a sharp tip 11a at its distal end such that it can easily penetrate the heart septum 4 under an appropriate rotation with a simultaneous motion axially forward.

Figure 8:
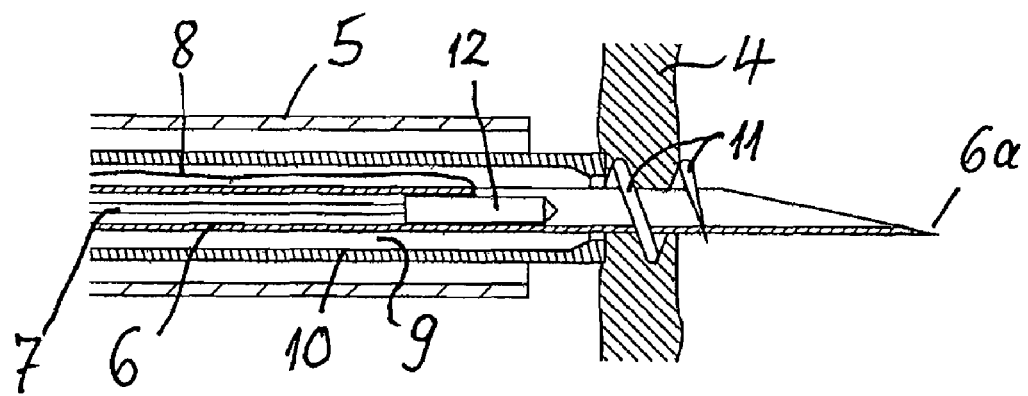
FIG. 8: an illustration according to FIG. 7 after the pushing forward of the puncture instrument and/or the puncture cannula through the screw catheter and the helical screw and after the penetration of the septum, with it during the penetration being held back by the helical screw and the screw catheter against the force applied during piercing and with the exiting length of the tip of the puncture cannula being selected sufficiently large to allow bringing the anchor, still located within the puncture cannula, behind the septum of the heart, with the feed catheter being shown in the longitudinal cross-section.
Figure 9:
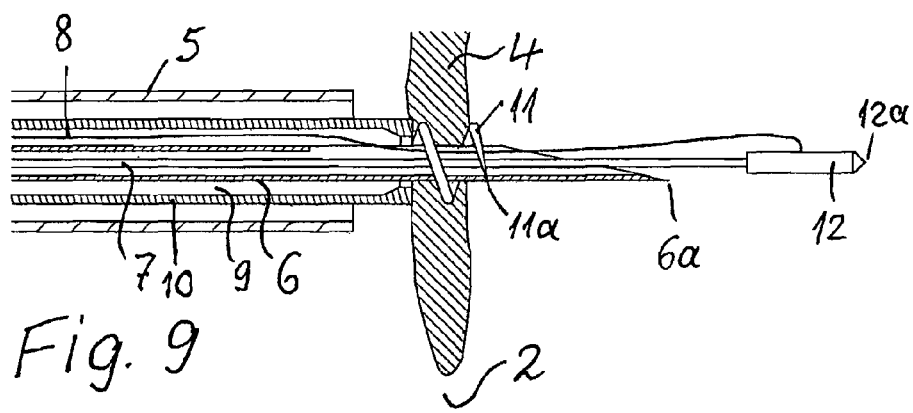
FIG. 9: an illustration according to FIG. 8 after the anchor has been pushed out, as in the situation shown in FIG. 6, with the anchor still engaging the tool.
Figure 10:
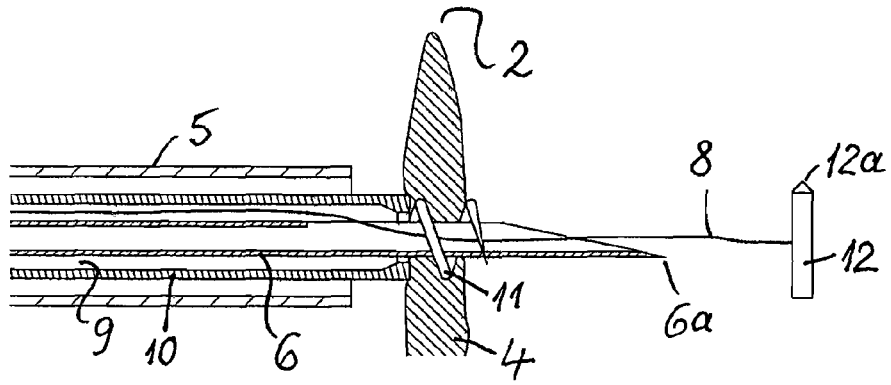
FIG. 10: an illustration according to FIG. 9 after the tool serving to push out the anchor has been pulled back.
Figure 35:
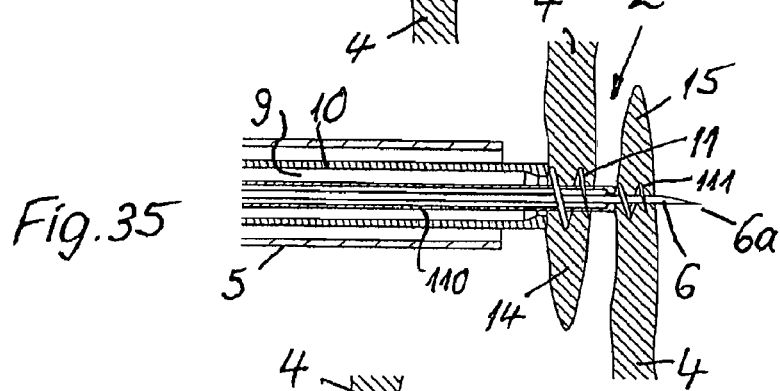
Figure 36:
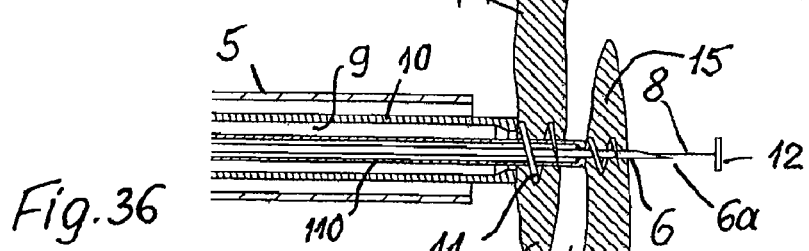

The relation of the lumen and/or the open interior cross-section of the screw catheter 10 in reference to the puncture cannula 6 is very well discernible in FIGS. 8 through 10 for the first embodiment and in FIGS. 35 and 36 as well as 39 and 40 for the second and third embodiment. Therefore, according to these illustrations, the tip 6a of the puncture instrument 6 can be pierced through the area of the heart septum 4 enclosed by the respective helical screw 11 in the position of use, in order to reach the position shown in FIG. 6, for example.

The screw catheter 10 can be engaged at its proximal end projecting from the feed catheter 5 and/or at a handle 13, by which it is operated, i.e. pushed forward through the feed catheter 5 and additionally can be rotated in order to rotate or screw the helical screw 11 into the septum 4. Further, the screw catheter 10, and its handle 13, serve to compensate the force which the puncture cannula 6 acts upon the heart septum 4 when penetrating the edge area of the opening 2. This way undesired or excessive deflection of the edge region can be prevented when the puncture cannulas 6 is pierced in. The operator can therefore pierce, on the one hand, the puncture cannula 6 through the heart septum 4 and, on the other hand, hold and fix the heart septum 4 with a comparable force at the handle 13 via the helical screw 11 and the screw catheter 10.

In the embodiments the helical screw 11 is provided with approximately one and one half windings or two windings, which according to FIGS. 7 through 10, 33 through 36 and 38 through 40 encompasses the point of the heart septum 4 to be punctured or to be pierced in the position of use. The incline of the respective helical screw 11 and a second helical screw 111 of FIGS. 33 through 40 is selected such that their tips 11a, 111a in the position of use project from the heart septum 4 at the side facing away from the feed catheter 5 or extending to the surface of said heart septum 4 facing away from the feed catheter 5. As a result, the heart septum 4 is always engaged and encompassed in its interior, in case of a projection of the helical screw 11 or 111 also at its exterior, such that the retention force transferred via the handle 13 and the screw catheter 10 can be well introduced to the heart septum 4.

Figure 7:
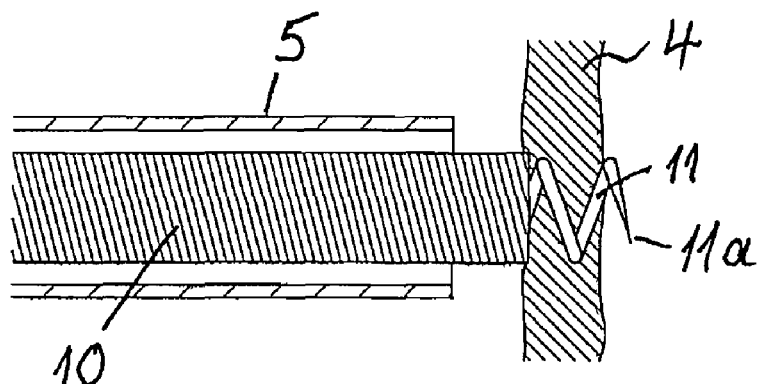
FIG. 7: in an enlarged view of, the distal end of the feed catheter and the screw catheter in the arrangement according to FIG. 5, with the distal end of the feed catheter and the screw catheter pushed forward therein being shown after the helical screw has been screwed into the septum.

The shaft of the respective screw catheter 10, 110 transferring the screw force is here flexible but not elastic or only slightly elastic, with its wall according to FIG. 7 possibly comprising one or more wires, which in form of closed helixes provide the necessary flexibility and simultaneously good axial stability.

Figure 37:
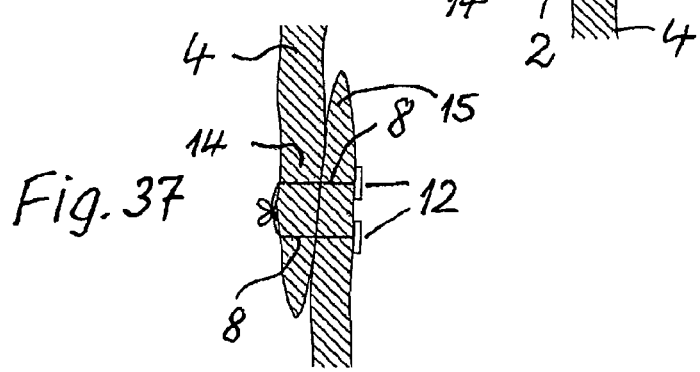

In the embodiments the closing elements already mentioned can be fastened via two anchors 12 provided with pulling means 8 at a distance from each other in the edge region of the opening 2 of the heart septum 4 via puncture cannulas 6, and their pulling means 8 can be knotted together in the position of use according to FIGS. 16, 17, 21, 22, 25, 26, and 37, producing an ASD-closure or according to FIG. 37 a PFO-closure.

While in the embodiments according to FIGS. 1 through 32 a device 1 for closing an opening 2 is shown, having an encircling edge, the FIGS. 33 through 40 show an arrangement in which the opening 2 in the heart septum 4 is provided with tissue flaps 14, 15 overlapping each other, which can be made to contact according to FIG. 37 by the closing device, thus closing the distance between them and thus the opening 2.

Figure 33:
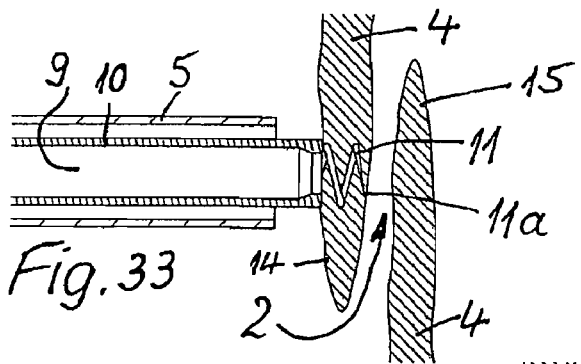
FIG. 33 through FIG. 37: the application of a modified embodiment of a device according to the invention for closing an opening formed in the heart by two tissue flaps arranged over top of each other or behind one another and here the distal end of the feed catheter and the screw catheter pushed forward therein after the helical screw has been screwed into the tissue flap located close to the guiding catheter.
Figure 34:
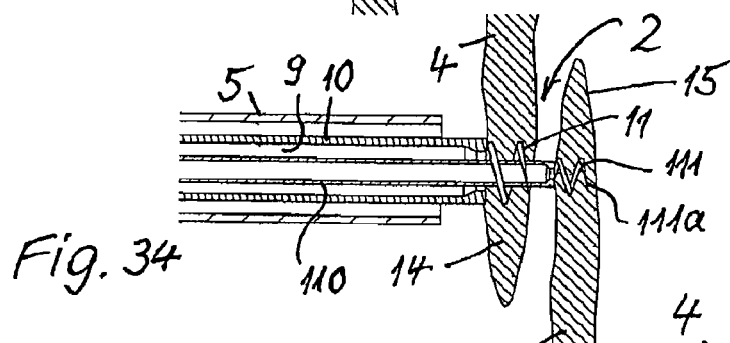

The device 1 for closing such an opening 2 formed by two overlapping tissue flaps 14 and 15 is provided, in addition to the already mentioned feed catheter 5, with a puncture cannula 6, a tool 7, and anchors 12 with pulling means 8 according to FIGS. 34 through 36 and the aforementioned second screw catheter 110, which fits into the first screw catheter 10, which in turn can be displaced through the feed channel 9 of the feed catheter 5. In FIGS. 34 through 36 this second screw catheter 110 is shown in the position of use and it is clear that it can not only be pushed through the first screw catheter 10 but it is also rotational in reference thereto, with the first screw catheter 10 with its helical screw 11 and can be screwed into the tissue flap 14 located closer to the guiding catheter 5 and subsequently the second screw catheter 110 can be screwed through it and the first tissue flap 14 into the second tissue flap 15, after the tissue flap, if necessary, has been punctured inside the helical screw in the manner not shown and has been dilated. The lumen or the open interior cross-section of the second screw catheter 110 and its helical screw 111 is again selected of such size that the puncture cannula 6 with the anchor 12 allocated to said closing device 1 and included therein and the tool 7 serving to operate the anchor 12 can be displaced in reference thereto and through said open interior cross-section and also through the second helical screw 111 into the area behind the second tissue flap 15. The individual steps for producing a PFO-closure with this modified device 1 are shown in FIGS. 33 through 37.

The second screw catheter 110 can also be fixed or engaged at its proximal end and its helical screw 111 can serve as a counter fastener and counter acts the force, which the puncture cannula 6 applies upon the rear tissue flap 15 when piercing it, keeping it from deflecting or retreating. The screw catheter 110 can be provided with two or more identical helical screws 111, off-set in the circumferential direction.

FIGS. 38 through 40 show a third embodiment, which also serves for a mutual approach and a connection of two tissue flaps 14, 15, with FIGS. 33 and 37 similarly relating to this embodiment as well. In this case, a suction tube or hose 16 is provided, which can be displaced by the first screw catheter 10 and its helical screw 11 and a puncture opening, not shown in greater detail, in the feed catheter 5 facing the first tissue flap 14 up to the second tissue flap 15 overlapping it, and with its proximal end it can be connected to a vacuum source. The respective situation is shown in FIG. 38.

Again, according to FIG. 33, the screw catheter 10 with its helical screw 11 is brought into position and anchored at the tissue flap 14 close to the feed catheter 5. Subsequently this tissue flap 14 is punctured in a manner not shown in greater detail and expanded at the punctured point by a dilator such that the suction tube 16 can be moved through it until its mouth has reached the rear tissue flap 15 according to FIG. 38. If a force is acted upon said rear tissue flap 15 it can be prevented from deflecting by a vacuum.

Here, as shown in FIG. 39, the suction tube or the suction hose 16 has an interior cross-section, through which the puncture cannula 6 with the anchor 12 included therein and allocated to the closing device 1 can be displaced in reference thereto and through said interior cross-section as well as through the second tissue flap 15. In this case, too, using the puncture cannula 6 an anchor 12 can be inserted into the heart septum 4, with the actual anchoring force once more being applied at pulling means 8. When piercing the puncture cannula into the tissue flap 15 said flap is prevented from deflecting or retreating by the suction tube and the vacuum applied.

The suction tube 16 can be fixed or engaged at its proximal end in a manner not shown in greater detail and based on the existing vacuum serve as a counter fastener and to counteract the force the puncture cannula 6 applies on the rear tissue flap 15 when piercing it.

In this case, similar to the embodiment according to FIGS. 33 through 37, at least two pulling means 8 can be mounted adjacent to each other as a closing element and can be connected and/or knotted at their ends facing away from their anchors 12, as shown in FIG. 37, which applies for the embodiment according to FIGS. 34 through 36 and for the embodiment according to FIGS. 38 through 40.

From the above-given description it is understood that primarily the anchors 12 with their pulling means 8 are important components of the device 1 according to the invention and/or of the set they form. According to FIGS. 3 and 4 the anchors 12 are embodied as pins and can be moved through the heart septum 4, with the help of the puncture cannula 6, and be stretched and have an engaging site for the aforementioned tool 7, for example a stylet, with a deformation being provided at the end of the tip 12a that can pierce or be guided through. The deformation can be coupled to the tool 7 in a detachable manner. The respective anchor 12 allocated to the device 1 is provided at its rear side in the feeding direction with a recess 17, open at its rear end and closed at the opposite end, for the engagement of the bar-shaped tool 7 or stylet fitting into said recess 17, with the anchor 12 can be moved out of the position, clearly shown in FIG. 2, inside the puncture cannula 7 and out of the feed catheter 5 and into or through the septum 4 of the heart 3, as for example shown in FIGS. 6 and 8 through 10, as well as 36 and 40. The operating handle 7a of the tool 7 is shown in FIGS. 2 and 3.

As shown in FIG. 4, the pulling means 8 each engage between the two ends of the pin-shaped anchor 12 approximately at its center.

Figure 11:
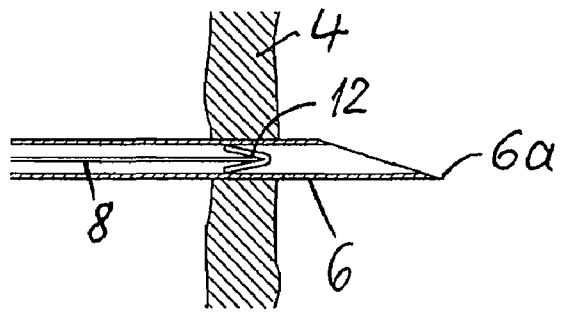
FIG. 11: a simplified illustration according to FIG. 8, with only the puncture element and a modified anchor located therein, comprising two folding parts, being shown as a pulling means.
Figure 12:
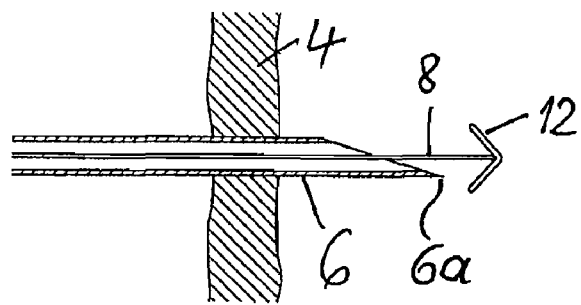
FIG. 12: an illustration according to FIG. 11 after the anchor according to FIG. 11 has been pushed out.
Figure 13:
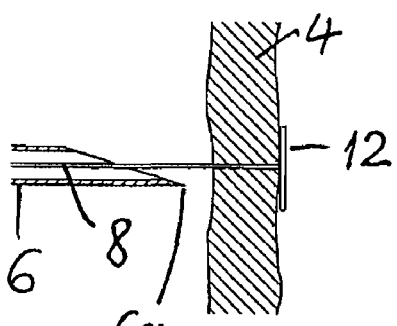
FIG. 13: an illustration according to FIGS. 11 and 12 after the puncture cannula has been pulled back and the anchor was made to contact the heart septum, through which the pulling means extend backwards.
Figure 18:
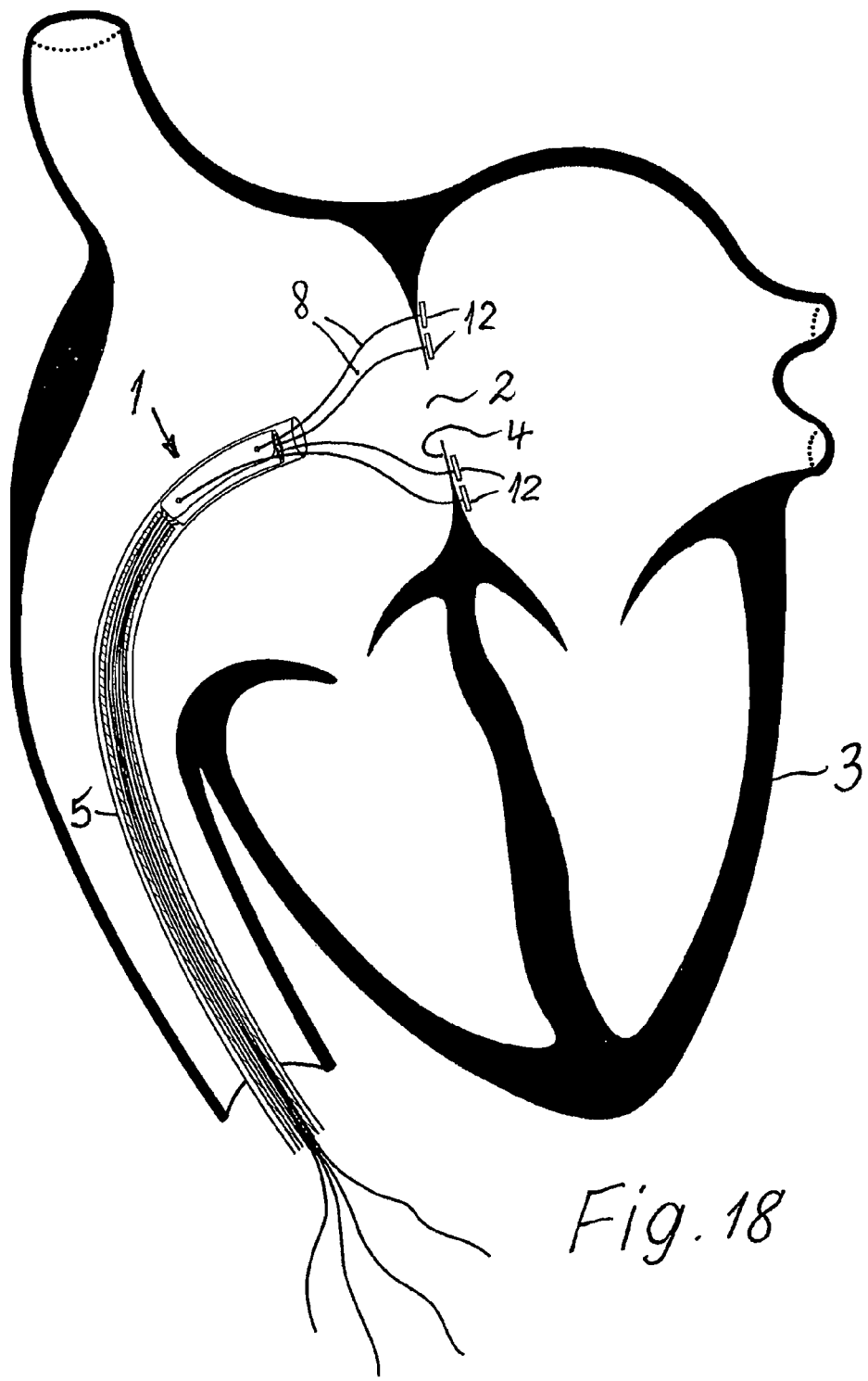
FIG. 18: an illustration of the heart similar to FIG. 6 in which the opposite edges of the opening in the septum of the heart are each provided with at least two anchors, before the opening is closed.

A modified embodiment for the anchor 12 is shown in FIGS. 11 through 13. The respective anchor 12 shown is flexible or folding opposite to its feeding direction in reference to the engagement point of the pulling means 8 and can therefore first be well stored inside the puncture cannula 6 according to FIG. 11 and then according to FIG. 12 be pushed out, by which it then begins to partially unfold. After the retraction of the puncture cannula and the application of force on the pulling means 8 for activating the closure then the anchor 12 facing away therefrom according to FIG. 13 contacts the heart septum 4 in a flush manner and can transfer appropriate anchoring forces.

Therefore, according to FIG. 2 as well as according to FIG. 11 the puncture cannula 6 accepts in its interior tool 7 and anchor 12, accepting said anchor 12 in its entirety or perhaps only partially in its interior. The pulling means 8 or the thread forming it in the arrangement of the anchor 12 according to FIG. 2 exit at their distal end within the puncture cannula 6 and extend at the outside of the puncture cannula 6 are being arranged there. The puncture cannula 6 projects from the anchor 12 held by it with its tip 6a, so that when inserting the anchor 12 first the tip 6a pierces the septum 4 adjacent to the opening 2 to be closed and punctures and perforates it such that the penetration of the anchor 12 is appropriately facilitated.

This way, with the help of the tool 7 engaging the recess 17 of the anchor 12, the anchor 12 can be moved out of the puncture cannula 6, and thus also out of the feed catheter 5, and be brought into its position of use.

The dimension of the interior cavity of the puncture cannula 6 according to FIG. 2, 35, or 39, at least in its exterior or distal end region, is approximately equivalent to the exterior cross-section of the anchor 12, for example, and accepts it entirely in its interior. The axial length of the anchor 12 can be determined by the tool 7.

It must be mentioned that the anchor 12 and the pulling means 8 are comprised of a non-metal material, particularly plastic.

Figure 6:
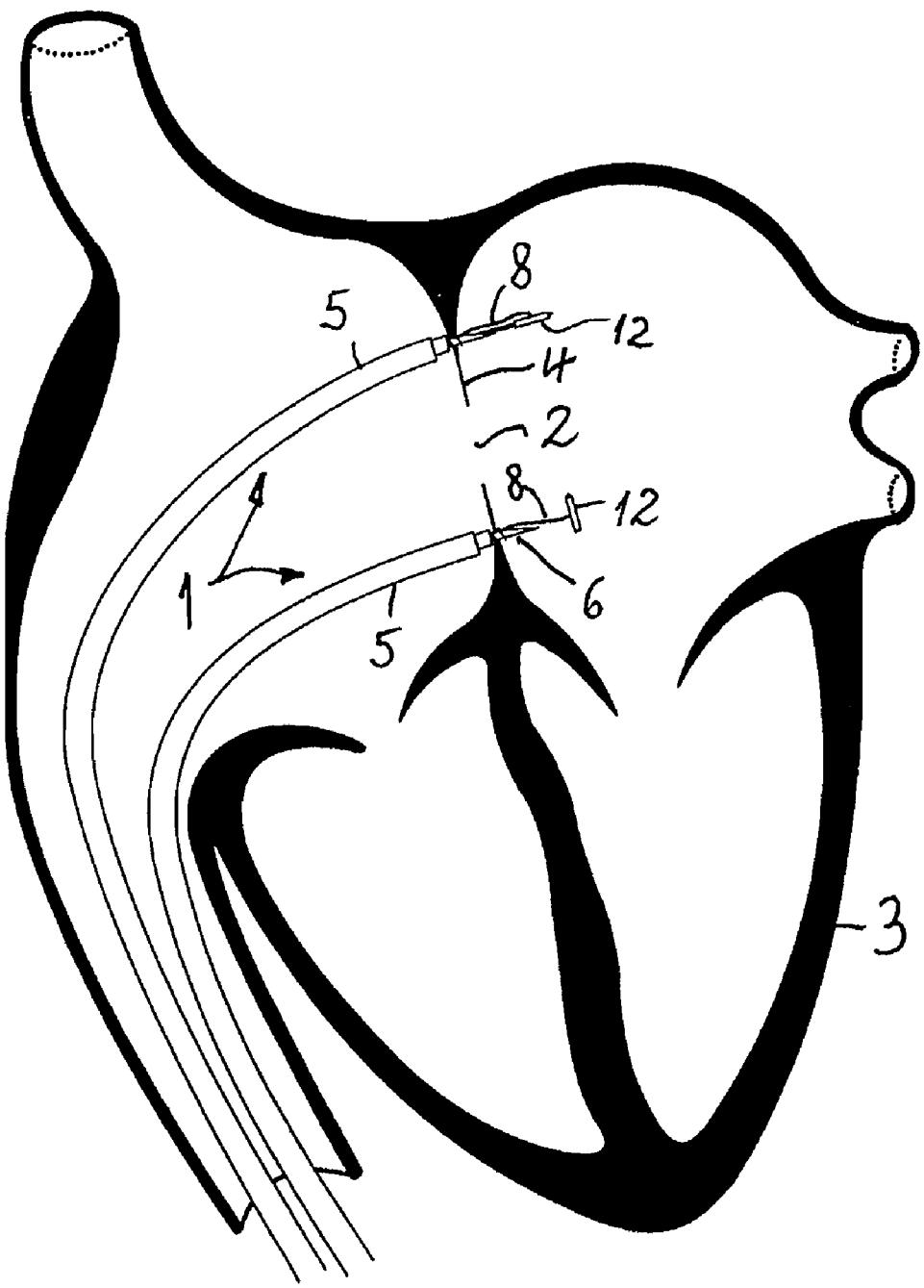
FIG. 6: an illustration according to FIG. 5 after the additional pushing forward of the puncture cannula through the screw catheter and after the septum has been pierced, with one anchor already having been pushed through the edge of the opening and being arranged perpendicular in reference to its pulling means, while the same or a second puncture cannula is pierced into the opposite edge of the opening to be closed between the left and the right atrium chambers, with the anchor shortly after its exit being oriented in the direction of the pulling means, with the two feeding steps for the two anchors being executed using two devices or successively using one device.

For example, if four anchors 12 are provided according to FIGS. 6, 14, and 15 in the edge region of the opening 2 located in the septum 4 of the heart 3, 2, pulling means or threads 8 each can be knotted to each other according to FIGS. 16 and 17 and be pulled together, causing the opposite edge regions of the opening 2 according to FIGS. 7 and 8 to approach each other and thus to close the opening 2 to such an extent that it can grow shut. This position can be fixed by the connection of the pulling means 8 with the help of knots 8a such that the opening 2 remains closed until it has grown shut. The knotting of the pulling means 8 can be carried out using conventional surgical means and methods.

According to FIGS. 18 through 22 the device and/or the set 1 can comprise or include, as parts of the closing element, at least two anchors 12 with the pulling elements or threads 12 being arranged each in the above-described manner thereat and at least one closing plate 18, which at least at its edge region having holes 19 for the pulling means 8 to pass through and through which the pulling means 8 or threads extend to the side of the closing plate 18 facing away from the opening 2 to be closed, where they are connected to each other or knotted in the position of use.

Figure 19:
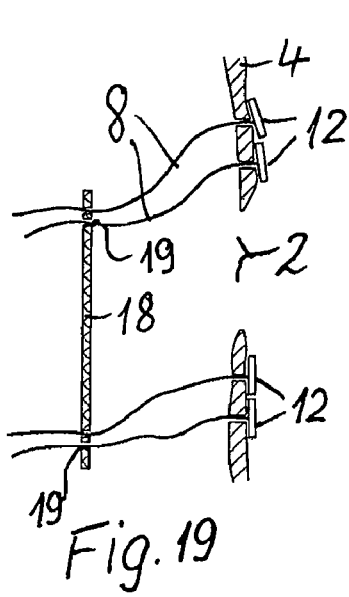
FIG. 19: an illustration according to FIG. 14, with the closing element, in addition to the anchors, having pulling elements or pulling means, being provided with a closing plate having holes, in order to allow its displacement via pulling elements into its position of use, with in FIG. 19 it still shows a distance from the opening in the heart septum to be closed.
Figure 20:
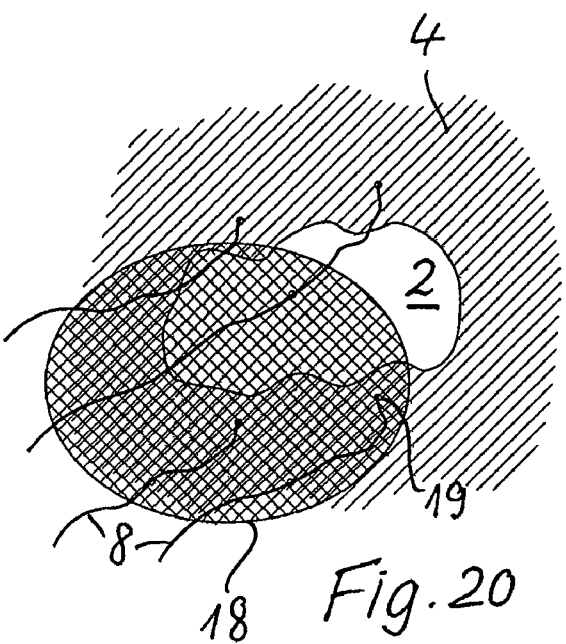
FIG. 20: a view of the opening in the heart septum according to FIG. 15, with four anchors having been previously mounted and the closing plate being displaced to a close proximity of the opening.
Figure 21:
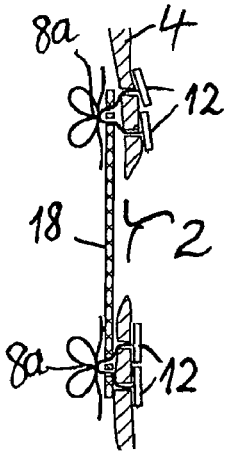
FIG. 21: an illustration according to FIG. 19 after the displacement of the closing plate up to it contacting the edges of the opening and after the mutual connection and knotting of the pulling means of the anchors at the side of the closing plate facing away from the opening.
Figure 22:
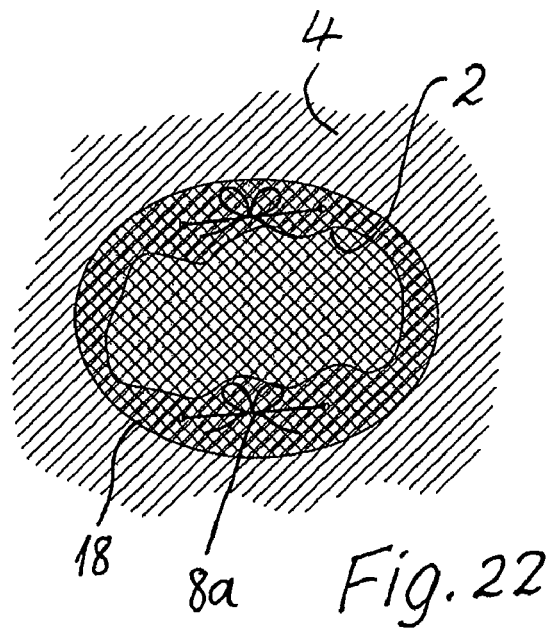
FIG. 22: an illustration according to FIG. 20 after the mounting of the closing plate in the position of use with the help of pulling means penetrating it.
Figure 23:
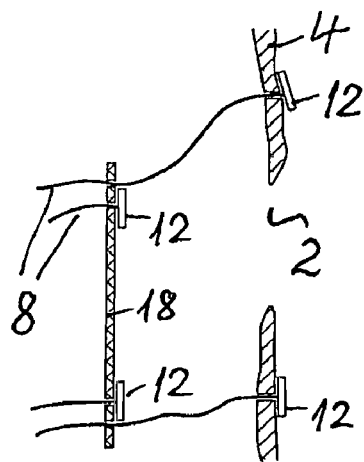
FIG. 23: an illustration according to FIG. 19, in which only two anchors are mounted at edges of the opening in the heart septum opposite each other, while two additional anchors immediately engage the closing plate.
Figure 24:
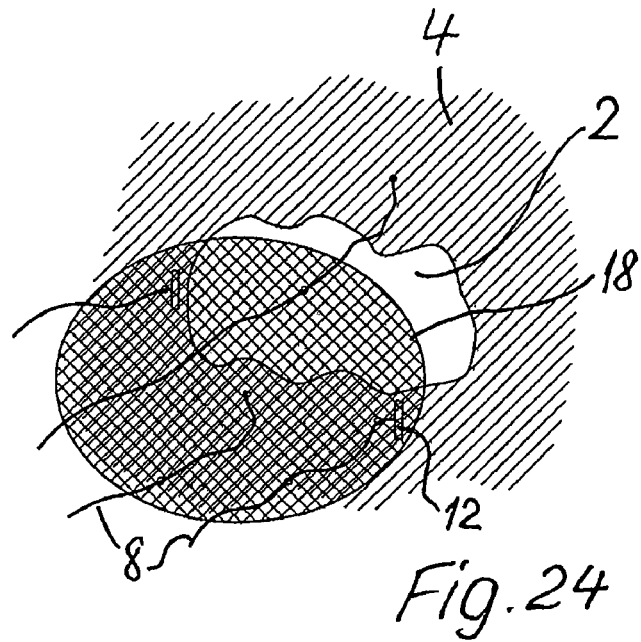
FIG. 24: an illustration according to FIG. 20, in which the closing plate still shows a distance from the opening in the heart septum.
Figure 25:
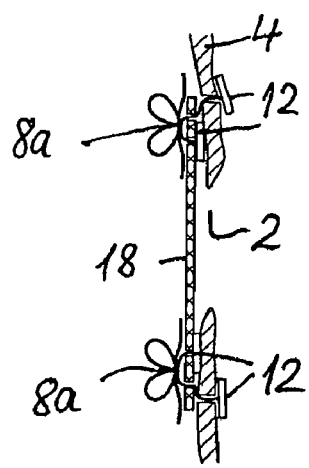
FIG. 25: an illustration according to FIG. 21 after the displacement of the closing plate up to its contacting the edges of the opening and after the mutual connection or knotting of the pulling means of one of them at the closing plate and one of the m at the anchor engaging the heart septum at the side of the closing plate opposite the opening.
Figure 26:
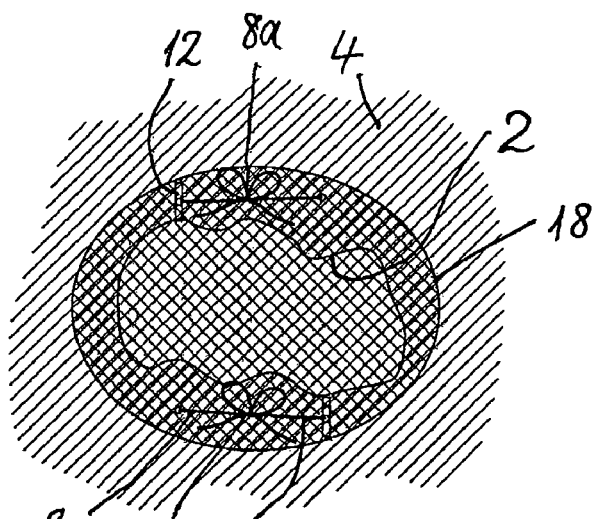
FIG. 26: an illustration according to FIG. 22 after the mounting of the closing plate according to FIGS. 23 through 25 in the position of use with the help of pulling means penetrating it.

For a particularly large opening 2 in the septum 4 in the heart 3 the device 1 can therefore comprise, in addition to the anchors 12, a closing plate 18, which can be guided in its position of use with the help of pulling means or threads 8 of the previously mounted anchors 12, shown in FIGS. 19 and 20. Therefore, first the anchors 12, in this embodiment a total of four anchors 12, placed successively with the help of the puncture cannula 6 in the manner described or also with the help of several puncture cannulas 6 in the edge region of the opening 2 in the septum 4, after which the closing plate 18 having holes 19 is pushed over the pulling means 8 and can be guided through it until it contacts the edge region of the opening 2 and covers and seals the opening 2 according to FIG. 22. Therefore, at least three or, according to FIG. 20, four anchors 12 and knots 8a forming pulling means 8 as well as one closing plate 18 can be provided as closing elements. For an even larger opening 2, more than four anchors 12 may be provided as well. The closing plate 18 is comprised of a non-metal material and can comprise a bio-compatible material or plastic similar to the anchor 12 and the pulling means 8. This way, metal parts are avoided and the risk of embolisms is reduced or avoided.

A modified embodiment of the closing plate 18 is shown in FIGS. 29 through 32. In this case, the closing plate 18 has initially no holes 19, but prepared reinforced areas 19a, at which optionally, as needed, holes 19 can be inserted. This way the closing plate, according to FIGS. 29 and 30 having an oval perimeter, according to FIGS. 31 and 32 a rectangular, square, or octagonal perimeter, adjusts as much as possible to the respective requirements and can be further adapted by trimming its edges to the shape of the opening 2.

As a closing element and/or a closing device in this case, a closing plate 18 is provided with several anchors and pulling means 8, where two anchors 12 each and their pulling means 8 can be connected or knotted to each other in the position of use. FIGS. 23 through 26 show a modified version such that in the edge region of the opening 2 two anchors 12 each are arranged in the heart septum 4 and two additional anchors 12 in the edge region of the closing plate 18, where in the position of use one pulling means 8 each of an anchor 12 contacting the heart septum can be knotted or is knotted to an anchor 12 cooperating with the closing plate 18. Therefore, again two closing knots 8a form, whereby only two anchors require mounting to the heart septum 4, while the two corresponding anchors reach the position of use together with the closing plate 18.

Figure 27:
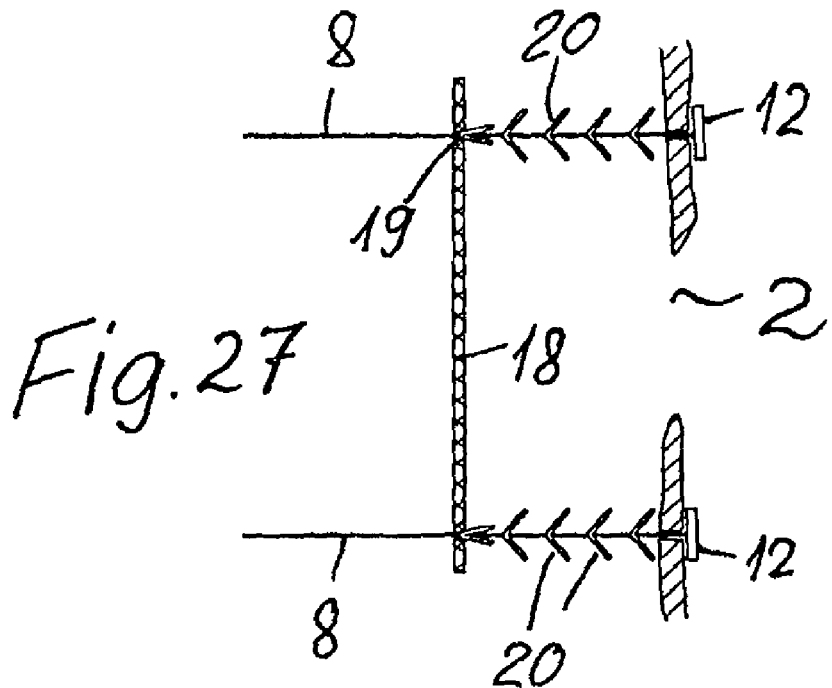
FIG. 27: an illustration according to FIG. 14 or 19, in which a closing plate is arranged at a distant from the opening in the heart septum on the pulling means of anchors, with the pulling means on the side of the heart septum facing away from the anchors being provided with barbed holders.
Figure 28:
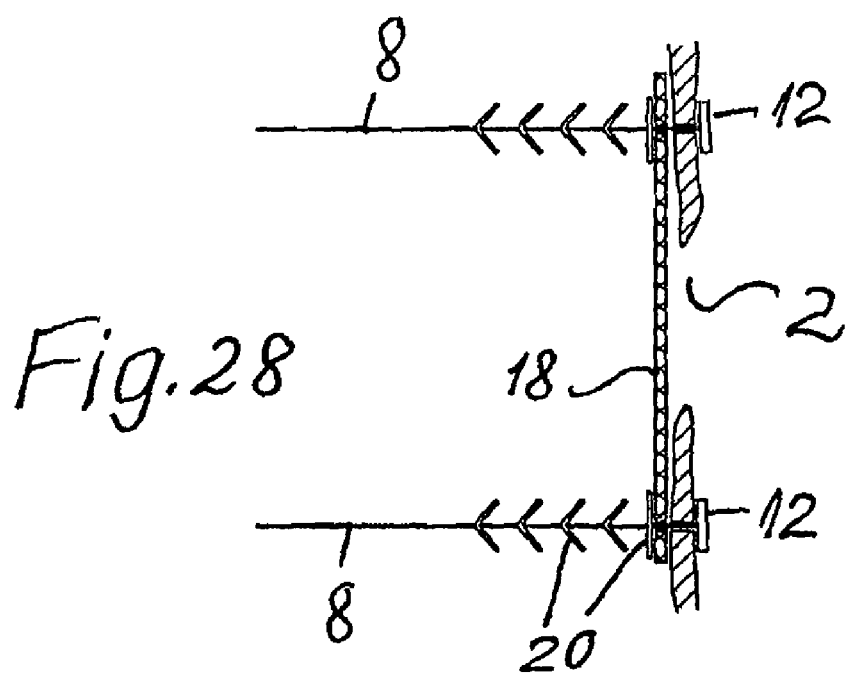
FIG. 28: an illustration according to FIG. 27 after the displacement of the closing plate up to its position of use in which it contacts the edges of the opening in the heart septum, with it being fixed by the barbed holding elements located closest to said separating wall.
Figure 29:
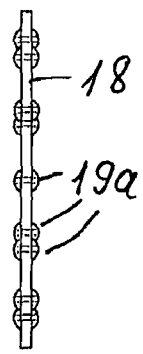
FIG. 29: a side view
Figure 30:
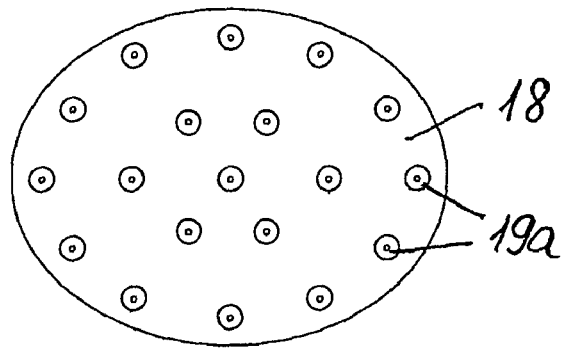
FIG. 30: a top view of a closing plate having places prepared and predetermined for punching holes, which can be pierced when necessary, with the closing plate showing an oval perimeter.
Figure 31:
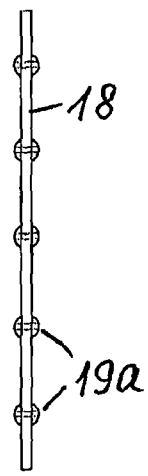
FIG. 31.
Figure 32:
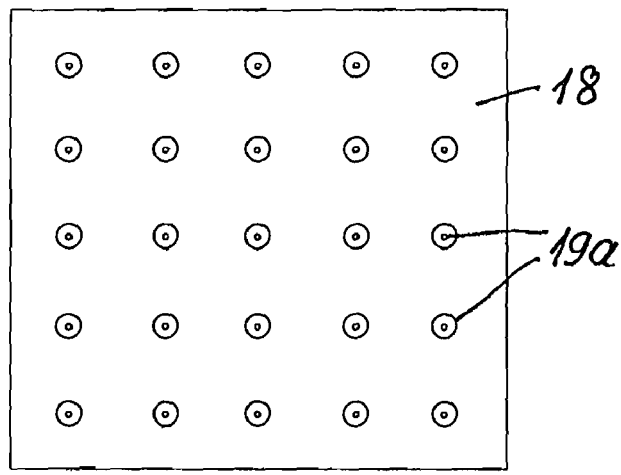
FIG. 32: the illustration of a closing plate according to FIGS. 29 and 30, with the closing plate showing a rectangular or square perimeter.

FIGS. 27 and 28 also show a way to fix a closing plate 18 with only two anchors 12, although more than two anchors 12 could be used. In the embodiment according to FIGS. 27 and 28 it is discernible that at least one barbed or bendable protrusion 20, in the embodiment several, is provided at the pulling means 8, distanced from the anchor 12, by which the holes 19 of the closing plate 18 can be displaced in the direction towards the respective anchor 12, but can be fixed in the direction opposite the insertion direction. FIG. 27 shows the closing plate 18 at a distance from the heart septum 4 and the opening 2, particularly a first pair of barbed protrusions 20 being folded to enter the respective hole 19 of the closing plate 18. In FIG. 28 the closing plate 18 has reached its position of use and is fixed by the pair of barbed protrusions 20 located closest to the heart septum 4 and the opening 2, which contact the side of the closing plate 18 facing away from the heart septum 4.

From the above-described embodiments a device 1 and/or a set results by which an opening 2 in a heart septum 4 can be effectively closed with few parts. The respective important anchors 12 for the closure can be moved through the respective area of the septum 4 without said area of the heart septum 4 being able to deflect because it can be fixed with the help of a helical screw 11 or 111 or with the help of a suction tube or hose 16.

A device or a set 1 serves to close an opening 2 in a separating wall 4 located in the heart 3 between two heart chambers with a multi-part closing element. A feed catheter 5 is important for a transvenous introduction of the closing element into the interior of the heart 3 and a puncture cannula 6 as well as a tool 7 or a stylet for pushing at least part of the closing element out of the distal end of the puncture cannula 6 after it has been penetrated through the edge or the neighboring section of the opening 2 located in the heart septum 4, with at least two individual elements being provided as closing elements, having pulling means 8 or threads, which can be pulled together, connected and/or knotted to close the opening 2 in the position of use. The device 1 is provided with at least one screw catheter 10 that can be pushed into the feed catheter 5 and moved forward through it with at least one helical screw 11 provided at its distal end that can be screwed into the edge region of the opening 2 in the heart septum 4, where the puncture cannula 6 has an anchor 12 for closing that can be displaced through the interior cross-section of the screw catheter 10 and the helical screw 11. The edges of the opening 2 overlap the flap 15 facing away of the feed catheter 5 and can be provided with at least a second helical screw 111 or a suction tube 16 against the force of the puncture cannula 6 when piercing and placing the anchors 12.

The invention claimed is:

1. A device (1) for closing an opening (2) in a septum (4) in a heart (3) between two heart chambers, the device including a closing element, comprising a feed catheter (5) for transvenous introduction of the closing element into an interior portion of the heart (3) and a puncture cannula (6) and a tool (7) or stylet for pushing the closing element out of a distal end of the puncture cannula (6) after the cannula penetrates an edge or neighboring region of the opening (2) in the heart septum (4), at least two individual elements are provided as closing elements having pulling members (8) or threads, which to close the opening (2), in a position of use, are pulled together, connected, or knotted, a first screw catheter, (10) having an interior feed channel (9) that is inserted into the feed catheter (5), and at a distal end at least one helical screw (11; 111), configured to be screwed into the edge region of the opening (2) in the heart septum (4), the first screw catheter (10) comprising a helical screw (11) being selected of such size that the puncture cannula (6), with an anchor (12) allocated to the closing element and included therein, is displaced in reference thereto and through its interior cross-section as well as through the at least one helical screw (11), a second screw catheter (110) is provided, which fits into the first screw catheter (10), is pushed through it and is rotational in reference thereto, the first screw catheter (10) having at least one helical screw (11) is screwed into the tissue flap (14) located close to the guiding catheter and subsequently the second screw catheter (110) is screwed through the first tissue flap (14) into the second tissue flap (15), with the lumen or the open interior cross-section of the second screw catheter (110) and the at least one second helical screw (111) being selected of such a size that the puncture cannula (6) and anchor (12) contained therein and allocated to the closing device (1) is displaceable in reference thereto through its interior cross-section and through the at least one second helical screw (111) into an area behind the second tissue flap (15).

2. A device according to claim 1, wherein the first screw catheter (10) in the position of use is fixed or engaged at a proximal end thereof and the helical screws serve as counter fastener and counteracts a force the puncture cannula (6) applies on said septum when piercing the edge area of the opening (2) in the heart septum (4).

3. A device according to claim 1, wherein the at least one helical screw (11) is provided with at least one winding and in the position of use encompass the point of the heart septum (4) to be punctured.

4. A device according to claim 1, wherein an incline of the at least one helical screw (11, 111) is selected such that a tip (11a; 111a) in the position of use projects from the heart septum (4) at a side facing away from the feed catheter (5) or reach to a surface of the heart septum (4) facing away from the feed catheter (5).

5. A device according to claim 1, wherein a shaft of the screw catheters (10; 110) transferring the screw force is flexible but only slightly elastic or not at all.

6. A device according to claim 1, wherein a wall of the screw catheters (10; 110) is a helix formed by at least one wire.

7. A device according to claim 1, wherein there are at least two of the anchors (12) having pulling members (8) arranged as closing elements at a distance from one another at the edge region of the opening (2) of the heart septum (4) via a puncture cannula (6) and the pulling members (8) are knotted to each other in the position of use.

8. A device according to claim 1, wherein the second screw catheter (110) is fixable or engageable at a proximal end and the at least one helical screw serves as a counter fastener and counteracts a force of the puncture cannula (6) upon the rear tissue flap (15) when penetrating it.

9. A device according to claim 1, wherein the anchors (12) are pin-shaped and are penetrateable through the heart septum (4) and guidable through it, and have a deformation arranged at the end opposite a piercing or penetrating tip (12a) of the anchor as the engagement point for a tool (7) or a stylet, the deformation comprising a recess (17) open at an end opposite a tip and ending at an inside portion, which can be detachably coupled to the tool (7), the tool or stylet fitting into said recess (17), and the pulling members (8) each engage between the two ends approximately in the middle between the two ends of the pin-shaped anchors (12).

10. A device according to claim 1, wherein the anchor (12) is flexible or foldable against a direction of insertion in reference to the engagement site of the pulling members (8).

11. A device according to claim 1, wherein the puncture cannula (6) accepting the tool (7) and the anchor (12) in an inner portion accept the anchor (12) entirely or partially, with the pulling member (8) or the thread, when the anchor (12) is arranged inside the puncture cannula (6), exits at a distal end and is arranged at an exterior portion of the puncture cannula (6).

12. A device according to claim 1, wherein the puncture cannula (6) projects the anchor (12) held by it with a tip (6a).

13. A device according to claim 1, wherein the anchor and the pulling member are comprised of a non-metal material.

14. A device according to claim 1, wherein the closing device comprises at least two anchors with pulling members and at least one closing plate (18), which at an edge region thereof has holes (19) penetratable by the pulling members (8) and through which the pulling members (8) extend to a rear portion of the closing plate (18) facing away from the opening (7) to be closed, where they are connectable to one another in the position of use or are knottable.

15. A device according to claim 14, wherein the closing plate is comprised of a bio-compatible or non-metal material.

16. A device according to claim 14, wherein at least one bendable or barbed protrusion (20) is provided at the pulling members (8) at a distance from the anchor (12), by which the holes (19) of the closing plate (18) can be displaced in the direction towards the anchor (12) but are fixable in the opposite insertion direction.

17. A device according to claim 1, wherein at least three anchors and pulling members and a closing plate are provided as the closing device.

18. A device according to claim 1, wherein the anchor is a flexible angular or barbed part, which is positioned in reference to the pulling members or thread when a pulling force is acting against the insertion direction or blocks the retraction of the pulling members or thread through a hole or a section of the heart septum.

19. A device (1) for closing an opening (2) in a septum (4) in a heart (3) between two heart chambers, the device including a closing element, comprising a feed catheter (5) for transvenous introduction of the closing element into an interior portion of the heart (3) and a puncture cannula (6) and a tool (7) or stylet for pushing the closing element out of a distal end of the puncture cannula (6) after the cannula penetrates an edge or neighboring region of the opening (2) in the heart septum (4), at least two individual elements are provided as closing elements having pulling members (8) or threads, which to close the opening (2), in a position of use, are pulled together, connected, or knotted, at least one screw catheter (10; 110), having an interior feed channel (9) that is inserted into the feed catheter (5), and at a distal end at least one helical screw (11; 111), configured to be screwed into the edge region of the opening (2) in the heart septum (4), the screw catheter (10) comprising a helical screw (11) being selected of such size that the puncture cannula (6), with an anchor (12) allocated to the closing element and included therein, is displaced in reference thereto and through its interior cross-section as well as through the at least one helical screw (11), wherein for closing an opening in a heart formed by two tissue flaps (14, 15) arranged on top of each other, a suction tube or hose (16)

is provided, which is displaceable through the at least one screw catheter (10) and the at least one helical screw (11) and a puncturing opening in the first tissue flap (14) facing the feed catheter (5) to the second tissue flap (15) overlapping it and which can be connected with a proximal end thereof to a vacuum source.

20. A device according to claim 19, wherein the suction tube or the suction hose (16) has an interior cross-section through which the puncture cannula (6) with the anchor (12) included therein and allocated to the closing device (1) is displaceable in reference thereto and through said interior cross-section as well as through the second tissue flap (15).

21. A device according to claim 19, wherein the suction tube (16) is fixable or engageable at a proximal end and based on the vacuum applied serves as a counter fastener and counteracts a force of the puncture cannulas (6) on the rear tissue flap (15) during piercing.

22. A device according to claim 19, wherein at least two pulling members are mountable adjacent to each other as closing elements and are connectable or knottable at ends that face away from the anchors (12).

* * * * *